(12) United States Patent
Bleakman et al.

(10) Patent No.: US 6,245,521 B1
(45) Date of Patent: *Jun. 12, 2001

(54) ASSAY FOR EVALUATING THE AFFINITY OF COMPOUNDS TO THE GLUTAMATE GLUR5 RECEPTOR

(75) Inventors: David Bleakman, Zionsville; David Lodge, Indianapolis, both of IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/262,859

(22) Filed: Mar. 3, 1999

(51) Int. Cl.[7] .......................... G01N 33/53; G01N 33/00; A61K 31/42
(52) U.S. Cl. ................ 435/7.1; 436/92; 514/380
(58) Field of Search ............ 435/7.1; 514/380; 436/92

(56) References Cited

U.S. PATENT DOCUMENTS

| 5,565,580 | 10/1996 | Wätjen ................................ 548/456 |
| 5,721,234 | 2/1998 | Bigge et al. ......................... 514/250 |
| 5,731,348 | 3/1998 | Gu ....................................... 514/561 |

FOREIGN PATENT DOCUMENTS 2316616   3/1998   (GB) .

OTHER PUBLICATIONS

Wahl, et al., Pharmacology and Toxicology of ATOA an AMPA receptor antagonist and a partial agonist at GluR5 receptors, neuropharmacology, Sep. 1998. vol. 37, pp. 1205–1210.

Proctor, Actions of Kainate and AMPA Selective Glutamate Receptor Ligands on Nociceptive Processing in the Spinal Cord, Neuropharmacology, Sep. 1998, vol. 37, pp. 1287–1297.

Vignes, et al., The GluR5 subtype of kainate receptor regulates excitatory synaptic transmission in areas CA1 and CA3 of the rat hippocampus, Neuropharmacology, (1998) vol. 37, pp. 1269–1277.

Stensbøl, et al., Resolution, absolute Stereochemistry and molecular pharmacology of the enantiomers of ATPA, European Journal of Pharmacology, (1999), vol. 380, pp. 153–162.

Clarke, et al., A hippocampal GluR5 kainate receptor regulating inhibitory synaptic transmission, Nature, vol. 389, Oct. 9, 1997, pp. 599–603.

Carroll, et al., Regional distribution of low affinity kainate receptors in brain of Macaca fascicularis determined by autoradiography using [3H](2S,4R)–4–methylglutamate, Neuroscience Letters, vol. 255, (1998), pp. 71–74.

Thomas, et al., Pharmacological differentiation of kainate receptors on neonatal rat spinal motoneurones and forsal roots, Neuropharmacology, vol. 37, (1998), pp. 1223–1237.

Johansen, et al., Synthesis of Deuterium and Tritium labelled (RS)–2–Amino–3–(5–tert–butyl–3–hydroxy–4–isoxazolyl)–propionic Acid (ATPA), a selective Kainic Acid Receptor Agonist, Journal of Labelled Compounds and Radiopharmaceuticals, vol. 42, (1999), pp. 937–947.

Bleakman[*]and Hoo[†], A high radioligand selective for the GluR5 kainate receptor , Life Science News 3, 1999 Amersham Pharmacia Biotech, pp. 10, [*]Eli Lilly and Company, Indianapolis, IN; [†]Allelix Biopharmaceuticals, Mississauga, Ontario Canada.

Primary Examiner—William R. A. Jarvis
(74) Attorney, Agent, or Firm—Alexander Wilson

(57) ABSTRACT

A hippocampal GluR5 receptor modulator, 2-amino-3-(3 2-amino-3-(3-hydroxy-5-tert-butylisoxazol-4-yl)propanoic acid (ATPA) is useful in methods of measuring the binding affinity of chemical compounds to GluR5 receptors.

2 Claims, No Drawings

ASSAY FOR EVALUATING THE AFFINITY OF COMPOUNDS TO THE GLUTAMATE GLUR5 RECEPTOR

This invention relates to a method of treating psychiatric disorders including cognitive disorders and assays for compounds having such activity.

BACKGROUND OF THE INVENTION

It is well known that excitatory neurotransmission in the mammalian central nervous system is primarily mediated by the amino acid, L-glutamate, acting on ionotropic and metabotropic receptors. Glutamate can act at three types of ionotropic glutamate receptors, (R,S)-2-amino-3-(3-hydroxy-5-methylisoxazol-4-yl) propanoate (AMPA), kainate (KA) and N-methyl-D-aspartate (NMDA) receptors (Hollman and Heinemann, 1994, *Annu. Rev. Neurosci.* 17; 31–108). Molecular biological studies have established that AMPA receptors are composed of subunits (GluR 1–4) that can assemble to form functional channels. Five kainate receptors, classified as either high affinity (KA1 and KA2) or low affinity (Glur5, GluR6, and GluR7) kainate receptors have been identified (Bleakman et al., 1996, *Mol. Pharmacol.* 49, No. 4; 581–585).

It is well established that the hippocampus is important in learning and memory (Squire, 1992, *Psychol. Rev.* 99; 195–231) and it is considered that such cognitive functions are mediated by plastic changes in glutamatergic transmission within the hippocampus involving AMPA, NMDA and metabotropic receptor activation (Bliss and Collingridge, 1993, *Nature,* 361, 31–39). An example of such a plastic change is long term potentiation which can be demonstrated using standard electrophysiological methods in vivo, and in vitro, in hippocampal slices. Recently, it has been reported that kainate modulates neurotransmitter release in the hippocampus (Chittajullu et al., 1995, *Nature* 379, 78–81), but it remains unclear which receptors underlie this modulating effect of kainate.

We have presently discovered that compounds having activity at one of the kainate receptor subtypes, namely GluR5, modulate synaptic transmission within the hippocampus. Such compounds thus have potential for altering cognitive functions and are therefore indicated for the treatment of cognitive disorders.

One such compound having activity at the GluR5 receptor is ATPA (2-amino-3-(3-hydroxy-5-tert-butylisoxazol-4-yl) propanoic acid). ATPA is a known compound (Lauridsen et al., 1985; *J. Med. Chem.* 28: 668–672) and was hitherto regarded as a selective AMPA receptor agonist (Krogsgaard-Larsen et al.,1996, *Eur.J. Med. Chem.* 31: 515–537). We have discovered that ATPA is a potent GluR5 ligand with nanomolar activity on human GluR5 in binding studies, and is more than 1000-fold less potent on other human AMPA and kainate receptors. Furthermore, in electrophysiological studies we have discovered that ATPA is a potent GluR5 agonist with micromolar activity on human GluR5 and rat DRG neurons and is 100-fold less potent on other human AMPA and kainate receptors.

It i s also well known that the hippocampus is involved in many other physiological and pathological functions (Kato, N. (ed) 1996, *The Hippocampus: Functions and Clinical Relevance.* Elsevier, Amsterdam). Importantly the hippocampus is involved in convulsive disorders (Dingledine et al., 1990 *TIPS* 11, 334–338) and is subject to neurodegeneration as a result of ischaemic, hypoxic, and hypoglycemic episodes (Meldrum and Garthwaite, 1990 *TIPS* 11; 379–387).

It is also well known that GluR5 receptors are distributed in other parts of the brain (Bettler et al., 1990, *Neuron* 5; 583–595).

It is further known that kainate receptors are located on dorsal root fibers and dorsal root ganglion neurons. ATPA is a potent agonist on these neurons which conduct nociceptive information into the spinal cord.

Thus, the present invention relates to methods of treating psychiatric and neurological disorders by administration of a compound that modulates the GluR5 receptor. Further, the present invention relates to assays for the identification of compounds that modulate the GluR5 receptor.

The treatment of mammalian psychiatric and neurological disorders is hereby furthered.

SUMMARY OF THE INVENTION

The present invention provides a method of treating a cognitive disorder which comprises administering to a patient in need thereof, a compound that modulates the GluR5 receptor in the hippocampus. Further, the present invention provides a method of treating a cognitive disorder which comprises administering to a patient in need thereof, a compound that shows selectivity for the GluR5 receptor, preferably ATPA, or a pharmaceutically acceptable salt thereof.

The present invention also provides a method of evaluating the binding activity of a test compound to recombinant or native GluR5 receptors, which method comprises; treating a sample containing recombinant or native GluR5 receptors with a measured quantity of the test compound; adding a measured quantity of labeled ATPA, or a salt thereof; and assaying the binding activity by measurement of the amount of labeled ATPA bound and test compound displaced.

Also provided in the present invention is a method of evaluating the effectiveness of a test compound for use in treating cognitive, psychiatric, or neurological disorders, which method comprises; measuring the binding affinity of the test compound to GluR5 receptors in the hippocampus or other tissue; and selecting the test compound according to its binding affinity to GluR5, relative to ATPA.

Additional methods provided in the present invention include a method of treating pain, or a neurological or psychiatric disorder, which method comprises administering to a patient in need thereof, a compound that modulates the GluR5 receptor in the hippocampus. Further, the present invention provides a method of treating pain, or a neurological or psychiatric disorder which comprises administering to a patient in need thereof, a compound that shows selectivity for the GluR5 receptor, preferably ATPA, or a pharmaceutically acceptable salt thereof.

DETAILED DESCRIPTION OF THE INVENTION

Activity of compounds acting at the kainate receptor, GluR5, can be determined by radiolabeled ligand binding studies at the cloned and expressed human GluR5 receptor (Korczak et al., 1994, *Recept. Channels* 3; 41–49), and by whole cell voltage clamp electrophysiological recordings of currents in acutely isolated rat dorsal root ganglion neurons (Bleakman et al., 1996, *Mol. Pharmacol.* 49; 581–585). The selectivity of compounds acting at GluR5 receptors is determined by measurement of activity at other AMPA and kainate receptors including receptor-ligand binding studies and whole-cell voltage clamp electrophysiological recordings of functional activity at human GluR1–GluR4 receptors (Fletcher et al., 1995, *Recept. Channels* 3; 21–31), at human GluR6 receptors (Hoo et al., *Recept. Channels* 2;327–338), at AMPA receptors in acutely isolated cerebellar Purkinje neurons (Bleakman et al., 1996, *Mol. Pharmacol.* 49; 581–585), and other tissues expressing AMPA receptors (Fletcher and Lodge, 1996, *Pharmacol. Ther.* 70; 65–89).

As stated, one compound having activity at the GluR5 receptor is ATPA. The present invention provides that ATPA is a potent GluR5 ligand with nanomolar activity on human GluR5 in binding studies, and is more than 1000-fold less potent on other human AMPA and kainate receptors. Furthermore, the present invention provides that in electrophysiological studies, ATPA is a potent GluR5 agonist with micromolar activity on human GluR5 and rat DRG neurons and is 100-fold less potent on other human AMPA and kainate receptors. The results of these selectivity binding studies and the results of these electrophysiological studies are described in detail, in Table 1 and Table 2 below:

TABLE 1

ATPA Selectivity Profile in Binding Studies

Cell lines (HEK293 cells) stably transfected with human GluR receptors were employed. Displacement of $^3$[H] AMPA by increasing concentrations of ATPA was used on GluR1–4-expressing cells and $^3$[H] kainate (KA) on GluR5, 6, 7 KA2-expressing cells. Estimated activity (Ki) in nM was as follows.

| GluR1 | GluR2 | GluR4 | GluR5 | GluR6 | GluR7 | KA2 |
|---|---|---|---|---|---|---|
| 17590 | 38616 | 15747 | 3.1 | >1 mM | 14319 | 38832 |

TABLE 2

ATPA Selectivity Profile in Electrophysiological Studies

Functional studies were carried out on HEK293 cells stably transfected with human GluR receptors and on acutely isolated dorsal root ganglion neurons (DRG) using patch-clamp technology (Bleakman et al., 1996, *Mol. Pharmacol.*, 49, 581–585). EC50 values (m$\mu$) for ATPA were estimated for GluR1–4 vs 100 m$\mu$AMPA, GluR5 vs 100 m$\mu$ KA, GluR6 vs 1 m$\mu$ KA, and DRG vs 30 m$\mu$ KA, with the following results:

| GluR1 | GluR2 | GluR3 | GluR4 | GluR5 | GluR6 | DRG |
|---|---|---|---|---|---|---|
| >300 | >300 | >300 | >300 | 4 ± 0.7 | >300 | 0.56 ± 0. |

Thus, the present invention provides that ATPA is highly selective at the GluR5 receptor. Preferred compounds useful in the present invention have a binding activity at the GluR5 receptor of at least 10-fold that at any of the remaining glutamate receptors.

It is clear that the newly discovered properties of ATPA make it a useful research tool for identifying physiological processes mediated by GluR5 and for the investigation of chemical compounds having potential activity at the GluR5 receptor. The present invention, therefore, encompasses the use of ATPA, or labeled ATPA, or a salt thereof, in biological tests which enable the discovery of the activity of chemical compounds at GluR5 receptors. Such biological tests include ligand binding displacement studies, activity in in vitro and in vivo preparations, and the localization of GluR5 receptors in tissue samples.

Thus, the present invention provides a method of assaying the binding activity of a chemical compound to recombinant or native GluR5 receptors, which method comprises treating a sample such as a fraction of a suspension or homogenate of tissue containing recombinant or native GluR5 receptors with a measured quantity of the chemical compound; adding a measured quantity of labeled ATPA, or a salt thereof; and assaying the binding activity by measurement of the amount of ATPA bound and chemical compound displaced. The ATPA reagent can be labeled by conventional means well known to the ordinarily skilled artisan, such as, by radiolabelling or pigment or dye, and can be assayed by techniques such as scintillation counting, or other conventional means. Preferably the concentration of ATPA employed in the assay is 100 nM or less.

In the absence of labeled ATPA, binding studies for screening compounds for GluR5 activity may be performed by assays in which ATPA-displaceable binding of another labeled compound with high affinity for the GluR5 receptor, is measured. Suitable labeled compounds for this assay include glutamate and kainate. Such assays may be best performed in the presence of compounds that block the binding to other glutamate receptors. A compound active at the GluR5 receptors modulates the remaining ATPA-sensitive binding.

In a further aspect of the present invention there is provided a method of screening a compound for binding affinity to GluR5 receptors which comprises measuring the binding affinity of the compound to GluR5 receptors in the hippocampus or other tissue expressing GluR5 receptors, and selecting the compound according to its binding affinity, relative to ATPA.

Other screening assays include functional tests for GluR5 activity including standard electrophysiological and calcium flux assays on recombinant or native GluR5 receptors, in which ATPA has known activity.

As mentioned above, ATPA modulates synaptic transmission in the hippocampus. In particular, in electrophysiological tests similar to those described in Chittajulu et al., 1995, *Nature* 379, 78–81, ATPA(1 $\mu$M) reduces synaptic inhibition onto $CA_1$ pyramidal neurons. This activity indicates that GluR5 receptors are important in facilitating excitatory synaptic transmission in the hippocampus. It is further believed that such selective modulation of GluR5 is likely to show benefits in the treatment of cognitive function. Thus, the preferred method of treatment of the present invention is one in which the compound administered shows selectivity for the GluR5 receptor.

A preferred method of the present invention is one for treating cognitive disorders such as memory and learning disorders, dementia, and amnestic disorders.

As mentioned previously, one compound having activity at the GluR5 receptor is ATPA (2-amino-3-(3-hydroxy-5-tert-butylisoxazol-4-yl)propanoic acid), and the present invention therefore encompasses a method of treating a cognitive disorder by administering ATPA, or a pharmaceutically-acceptable salt thereof.

Thus, the present invention provides a method for treating a cognitive disorder by administration of a compound that selectively modulates the GluR5 receptor in the hippocampus. The invention further provides the use of a compound that modulates the GluR5 receptor in the hippocampus, for the manufacture of a medicament for the treatment of such a cognitive disorder.

Further, as mentioned above, the hippocampus is also involved in many other physiological and pathological states such as convulsive disorders and is subject to neurodegeneration as a result of ischaemic, hypoxic, and hypoglycemic episodes. It is also well known that GluR5 receptors are distributed in other parts of the brain. Thus, the present invention encompasses the use of modulators of GluR5 function in the treatment of neurological and psychiatric disorders in which the hippocampus or other brain region is implicated and, in particular, in convulsive disorders and neurodegenerative diseases.

Finally, as mentioned above, it is known that kainate receptors are located on dorsal root fibers and dorsal root ganglion neurons. ATPA is a potent agonist on these neurons (see Table 2) which conduct nociceptive information into the spinal cord. The invention therefore includes the use of modulators of GluR5 function in the treatment of pain, and particularly of severe, chronic, intractable, or neuropathic pain.

It will be understood that the amount of the active compound administered to the patient will be determined by a physician, in the light of the relevant circumstances, including the condition to be treated, the chosen route of administration, the actual compound administered, the age, weight, and response of the individual patient, and the severity of the patient's symptoms. For example, dosages per day normally fall within the range of 0.1 to 50 mg/kg of body weight, and in the treatment of adult humans the range is usually from 1 to 15 mg/kg/day. These dosage ranges are not intended to limit the scope of the invention in any way, and in some instances dosage levels below the lower limit of the aforesaid range may be more than adequate, while in other cases still larger doses may be employed without causing any harmful side effect, provided that such larger doses are first divided into several smaller doses for administration throughout the day.

What is claimed is:

1. A method of evaluating the binding activity of a test compound to recombinant or native GluR5 receptors, which method comprises:

(a) treating a sample containing recombinant or native GluR5 receptors with a measured quantity of the test compound;

(b) adding a measured quantity of labeled ATPA, or a salt thereof; and (c) assaying the binding activity by measurement of the amount of labeled ATPA bound and test compound displaced.

2. A method of evaluating the effectiveness of a test compound for use in treating cognitive, psychiatric, or neurological disorders, which method comprises:

(a) measuring the binding affinity of the test compound to GluR5 receptors in the hippocampus or other tissue; and (b) selecting the test compound according to its binding affinity to GluR5, relative to ATPA.

* * * * *